United States Patent
Bhatt et al.

(10) Patent No.: US 7,439,062 B2
(45) Date of Patent: Oct. 21, 2008

(54) BEADS FOR CAPTURING TARGET CELLS FROM BODILY FLUID

(75) Inventors: Ram S. Bhatt, San Diego, CA (US); Pavel Tsinberg, Carlsbad, CA (US)

(73) Assignee: Biocept, Inc., San Diego, CA (US)

( * ) Notice: Subject to any disclaimer, the term of this patent is extended or adjusted under 35 U.S.C. 154(b) by 344 days.

(21) Appl. No.: 11/021,304

(22) Filed: Dec. 23, 2004

(65) Prior Publication Data

US 2006/0141045 A1   Jun. 29, 2006

(51) Int. Cl.
- C12N 5/00 (2006.01)
- C12N 11/02 (2006.01)
- C12N 11/08 (2006.01)
- C12N 11/06 (2006.01)
- C12Q 1/02 (2006.01)

(52) U.S. Cl. .................. 435/325; 435/29; 435/177; 435/180; 435/181

(58) Field of Classification Search .................. None
See application file for complete search history.

(56) References Cited

U.S. PATENT DOCUMENTS

| | | | |
|---|---|---|---|
| 3,551,555 A | 12/1970 | Schuurs | 424/12 |
| 3,553,310 A | 1/1971 | Csizmas | 424/2 |
| 3,939,123 A | 2/1976 | Matthews et al. | |
| 4,098,645 A | 7/1978 | Hartdegen et al. | |
| 4,110,286 A | 8/1978 | Vandegaer et al. | |
| 4,177,038 A | 12/1979 | Biebricher et al. | 8/192 |
| 4,675,286 A | 6/1987 | Calenoff | 435/7 |
| 5,240,602 A | 8/1993 | Hammen | 210/198.2 |
| 5,258,041 A | 11/1993 | Guire et al. | 623/66 |
| 5,378,624 A | 1/1995 | Berenson et al. | 435/239 |
| 5,447,842 A | 9/1995 | Simons | 435/6 |
| 5,503,981 A | 4/1996 | Mueller et al. | 435/7.21 |
| 5,641,628 A | 6/1997 | Bianchi | 435/6 |
| 5,714,325 A | 2/1998 | Bianchi | 435/6 |
| 5,766,843 A | 6/1998 | Asgari et al. | 435/5 |
| 6,008,040 A * | 12/1999 | Datar | 435/325 |
| 6,331,395 B1 | 12/2001 | Burchell et al. | 435/6 |
| 6,572,767 B2 | 6/2003 | Stipanovic et al. | 210/198.2 |
| 2002/0045196 A1 | 4/2002 | Mahoney et al. | 435/7.21 |
| 2002/0164825 A1 | 11/2002 | Chen | 436/526 |
| 2003/0134294 A1 | 7/2003 | Sandford et al. | |
| 2003/0153028 A1 | 8/2003 | Refseth et al. | 435/34 |
| 2003/0229393 A1 | 12/2003 | Kutryk et al. | |
| 2004/0018509 A1 | 1/2004 | Bianchi | |
| 2004/0069710 A1 | 4/2004 | Sirkar et al. | |
| 2005/0112650 A1 | 5/2005 | Chang et al. | |

FOREIGN PATENT DOCUMENTS

| | | |
|---|---|---|
| EP | 0355687 A2 | 2/1990 |
| WO | WO 91/16452 A1 | 10/1991 |
| WO | 94/26104 A1 | 11/1994 |
| WO | 00/65097 A1 | 11/2000 |
| WO | WO 02/081662 A1 | 10/2002 |

OTHER PUBLICATIONS

Gomez, S., et al.; "Capture of Rare Cells in Suspension with Antibody-Coated Polystyrene Beads"; Biotechnol. Prog. 1999, 15, 238-244; American Chemical Society and American Institute of Chemical Engineers (Published on Web Feb. 17, 1999).

Holzgreve et al., Fetal cells in the maternal circulation. J. Reprod. Med., 37:410-418 (1992).

Simpson et al., Isolating fetal cells from maternal blood. Advances in prenatal diagnosis through molecular technology. JAMA, 270:2357 (1993).

deKretser, T. A., et al., The separation of cell populations using monoclonal antibodies attached to sepharose. Tissue Antigens, 16:317-325 (1980).

Cuatrecasas, P., Protein purification by affinity chromatography. Derivatizations of agarose and polyacrylamide beads. J Biol Chem. 245(12):3059-65 (1970).

Mueller et al., Isolation of fetal trophoblast cells from peripheral blood of pregnant women. Lancet, 336:197-200 (1990).

Berenson, R. J. et al., Positive selection of viable cell populations using avidin-biotin immunoadsorption. J Immunol Methods. 91(1):11-9 (1986).

Bayer, E. A. et al., "The Avidin-Biotin Complex in Affinity Cytochemistry", in Methods in Enzymology, vol. 62, pp. 308-315 (1979).

Thomas, T. E., et al., Specific binding and release of cells from beads using cleavable tetrameric antibody complexes. J. of Immuno. Methods, 120:221-131 (1989).

\* cited by examiner

*Primary Examiner*—David M Naff
(74) *Attorney, Agent, or Firm*—Cooley Godward Kronish LLP

(57) ABSTRACT

Spheroidal beads present an exterior surface of a hydrophilic hydrogel, which is an isocyanate-functional polymer that is polymerized by urethane bonds and cross-linked by urethane and urea bonds. Sequestering agents present at the surface are covalently bound to isocyanate groups or to intermediate linkers that are so bound. These beads allow sequestering agents to retain their native three-dimensional configuration, and as a result of such surface characteristics and hydrophilicity, they achieve highly effective capture of very small subpopulations of rare cells from bodily fluids or the like and very effectively deter nonspecific binding of other biomaterials present in such bodily fluid. They may be all-hydrogel spheroids or hydrogel-coated substrates.

23 Claims, 1 Drawing Sheet

BEADS FOR CAPTURING TARGET CELLS FROM BODILY FLUID

This application relates generally to the separation of cells or the like from bodily fluids and more particularly to improved beads for cell separation and more efficient methods of separating cells or the like from bodily fluids using such beads.

BACKGROUND OF THE INVENTION

During pregnancy, a variety of cell types of fetal origin cross the placenta and circulate within maternal peripheral blood. Fetal cells have been detected in maternal circulation during certain stages of gestation (Holzgreve et al., 1992, *J. Reprod. Med.*, 37:410; Simpson, et al., 1993, *JAMA*, 270: 2357). Four fetal cell types in maternal blood that are accessible to prenatal diagnosis are lymphocytes, trophoblasts, stem cells and nucleated red blood cells. These cells provide a potential source of information about the gender and genetic makeup of the developing fetus. One particular fetal cell type within maternal blood that has been demonstrated to be useful for analyzing fetal DNA is the nucleated erythrocyte. The feasability of using fetal cells from the maternal circulation for diagnostic purposes, however, is greatly hindered by the fact that fetal cells are present in maternal blood in only very limited numbers. In addition, most fetal cells (with the exception of trophoblasts) cannot be distinguished from maternal cells on the basis of morphology alone; instead, identification must be based upon detection of either fetal cell markers or fetal DNA.

Detection of fetal cells in maternal blood can be improved by enrichment for fetal cells within the mixture of fetal and maternal cells and/or by separation of fetal cells from maternal cells. One approach that has been used to achieve enrichment for and separation of fetal cells within a maternal blood sample utilizes antibodies (Abs) specific for a particular fetal cell type to couple to and capture fetal cells or to label fetal cells. For example, as described in U.S. Pat. No. 5,641,628, fetal-specific, detectably labeled antibodies are used to label fetal cells and, when bound to these fetal cells, facilitate separation of these cells from maternal components by flow cytometry.

Another method of separating target cells from heterogenous cell populations in bodily fluids, such as blood, has been through the use of beds of particles which carry sequestering agents that are selected to capture a specific cell; examples of such sequestering agents are antibodies (Abs) that are directed at a ligand carried on the exterior surface of the target cells. The bodily fluid may be caused to flow through a stationary bed of such particles, or a group or bed of such particles may be caused to move, as by gravity, through a sample of the bodily fluid in question. Oftentimes this separation using such beads has taken place in a vertical column, and it is sometimes referred to as the "column" separation method. S. M. Gomez et al. in *Biotechnol. Prog.* 1999, 15, 238-244, use macroscopic polystyrene beads (100-170 microns) carrying CD45-Abs to separate a minor subpopulation of target cells from a large population of "bystander" cells.

There have been at least attempts to separate a fairly wide variety of cells by employing beads of this general type; particularly, beads have been used to separate fetal cells from maternal cells present in maternal blood of a pregnant woman. Such a method of separating target cells from a heterogenous population of cells suspended in a liquid medium is disclosed, for example, in International Application WO 94/26104. Moreover, U.S. Pat. No. 5,766,843 teaches the bonding of anti-CD45 antibodies to the exterior surface of solid supports, such as magnetic beads, which are then used to selectively bind to white blood cells. This patent also indicates that such beads coated with streptavidin are commercially available from Calbiochem and that antibodies to surface antigens on a wide variety of target cells may readily be attached thereto. U.S. Published Patent Application No. 2004/0018509 mentions the use of commercially available "Dynabeads" having magnetic cores, which are coated with antibodies, for removing placenta-derived trophoblast cells in the blood of pregnant women. Published Application 2003/0153028 mentions a number of types of polymeric beads that may be used as substrates to capture target cells of interest or to be removed from a blood sample.

U.S. Pat. No. 4,836,928 demonstrates the use of a separation device wherein the interior lumens of hollow fibers of an appropriate porosity are coated with a hydrogel made from polyvinyl alcohol that is mixed with a liposome dispersion and polymerized. It is said that the liposomes then capture B-cells as a bodily fluid is caused to flow through the hollow fibers; the B-cells are subsequently separately recovered by treatment with a buffer that releases them.

U.S. Published Patent Application 2003/0229,393 discloses the use of a medical device, such as a stent, which is coated with a bio-compatible hydrogel matrix that contains antibodies which capture progenitor endothelial cells for the purpose of forming an endothelium on the surface of the medical device.

U.S. Published Patent Application 2004/0018509, teaches obtaining fetal DNA by first depleting a blood sample of the maternal cells prior to fetal cell isolation and sorting. In order to enrich the eventual proportion of fetal cells present, the maternal cells are selectively removed by incubating the cells with antibodies attached to a solid support, which antibodies bind antigens present on the cell surface of mature leukocytes.

Published U.S. Application 2004/0069710 discusses various types of bioseparation-type devices, including some that have used adsorbent particles that bind target compounds which are moved through filters. It advocates large scale processing through a hybrid bioseparation apparatus that uses adsorbent particles, such as chromatographic matrix beads, to sequester the bioproducts after they pass through a membrane that is coated with a polymeric coating that is essentially impermeable to water, and to the biomolecules to be isolated.

From the number of different vendors who are marketing beads useful for this purpose, it is quite clear that there is very substantial interest in achieving the separation of biomolecules by the so-called column method. Accordingly, the search has gone on for improved solid supports, such as beads, that can be employed to selectively sequester biomolecules of interest.

SUMMARY OF THE INVENTION

The invention provides improved supports, particularly beads, for separating or isolating target cells or the like from a bodily fluid, or other liquid, which beads have an exterior surface which is hydrophilic and, in the presence of water, provides a highly porous surface region for excellently presenting sequestering agents. In one embodiment, the beads may utilize commercially available, biocompatible spheroids as substrates that are coated with an isocyanate-functional polyurethane hydrogel; in the presence of water, the coating provides a water-containing matrix of irregular exterior surface, the character of which is such that ligands can freely move into and out of this exterior surface region. In a second embodiment, the beads may be made entirely of hydrogel. Sequestering agents, such as Abs, are directly or indirectly, bonded to the hydrogel polymer at least at locations on or near the exterior surface, where they are available to couple with and thereby capture target cells from a bodily fluid, such as blood or other liquid. Because of the character of this swollen hydrogel surface, Abs which have been so bound will still retain their native configurations, and cell capture is greatly aided by this fact and by the particular hydrophilicity of the environment. Through the use of such improved beads, target cells can be very efficiently separated or isolated from a wide variety of bodily fluids or other liquids, and after washing, such cells can be released from capture and recovered for analysis or diagnosis purposes.

DETAILED DESCRIPTION OF THE PREFERRED EMBODIMENTS

Figure 1:
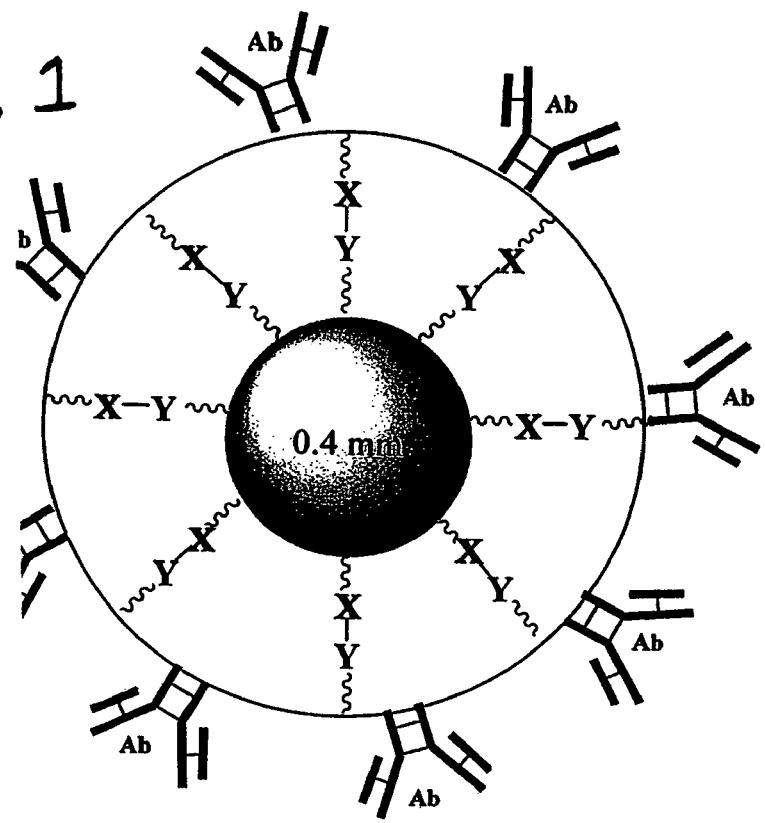
FIG. 1 shows a schematic representation of a plurality of sequestering agents, e.g. antibodies, covalently bonded to the exterior of a spheroidal, biocompatible bead in the form of a substrate which carries a swollen hydrogel-coating.
Figure 2:
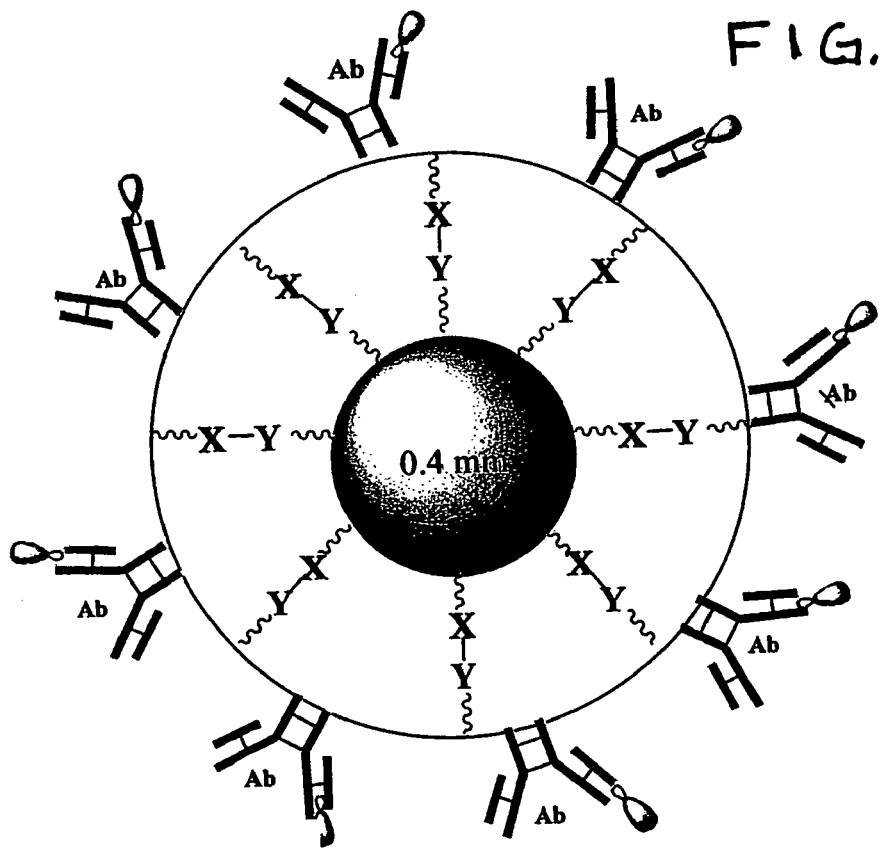
FIG. 2 shows cells having been captured by beads of FIG. 1.

In one aspect, the invention is based upon the discovery that, by coating a solid surface with a particular hydrogel, such solid surface can be transformed into one which is particularly suited for the attachment and subsequent presentation of sequestering agents. Alternatively, a comparable exterior surface can be provided by creating beads made substantially entirely from hydrogel. More particularly, the sequestering agents will be presented in their native, three-dimensional configuration in an hydrophilic environment at the surface, rendering them far more efficient to capture ligands to which they will normally couple, such as ligands that are present on the exterior surfaces of cells being targeted for isolation from a liquid, e.g. a bodily fluid such as blood. It is considered that any solid surface which is to be used for separation purposes can be improved in this manner; however, the invention is felt to have widespread applicability for providing beads, as beads have become the mechanism of choice for this purpose and have been widely used in what is referred to as the column separation method where antibody-coated beads or the like in a vertical column are contacted with the bodily fluid. Although the term "bead" is used throughout because this term has become known and accepted in this art, it should be understood that the term is considered to broadly cover particles in general less than about a centimeter in particle size. Although the term "cell" is used throughout this application, this term should be understood to include cell fragments and/or remnants that would likewise carry surface ligands specific to the sequestering agents.

When a solid support material is used as a substrate, it can be selected from any of a wide variety of biocompatible materials that are commonly used and commercially available. Particles such as plates, dishes and flasks (Corning Glass Works, Corning, N.Y.), meshes (Becton Dickinson, Mountain View, Calif.), membranes (Millipore Corp., Bedford, Mass.), particles, matrices, fibers and the like may be used; however, particles which are available from number of vendors including Amersham Biosciences, BioRad, and Sigma, are the substrates of choice, such as silica, cellulose, agarose, glass, and polymeric beads, both non-magnetic beads and magnetic beads.

Bio-Gel™ beads (Biorad, Richmond, Calif.) are marketed for separation purposes, and their polyacrylamide beads and cross-linked agarose beads may be used as spheroidal biocompatible substrates to be coated in Applicant's method of product preparation. Magnetic bead substrates will be preferred when it is desired to employ the straightforward application of a magnetic field to separate the beads from a supernatant. Such magnetic bead substrates, for example those sold as Dynal beads or those sold by Advanced Magnetics as BIO-MAG beads, can be used. Polystyrene beads are relatively inexpensive and are available commercially from Duke Scientific Corporation (Palo Alto, Calif.), Bangs Laboratories, Inc. (Fishers, Ind.), Polymicrospheres (Indianapolis, Ind.), and Argonaut Technologies (Redwood City, Calif.). It may sometimes be desirable to employ coated beads having a density close to that of the liquid to be treated, and substrates of appropriate density are then selected so that the hydrogel-coated beads will fall within a desired density range. For example, beads of a density of about 1.03 $gm/cm^3$ will provide suitable substrates for isolating cells from blood.

Such generally spherical beads are available in various size ranges from about 5 microns to 1 mm and may be used as substrates. Generally beads of at least about 10 microns are preferred for isolation methods. Usually, beads are used that are not larger than about 500 microns in diameter. Beads averaging about 200 to 400 microns in size may be more preferred for use in cell isolation methods.

Once a solid support has been selected for a substrate, the hydrogel coating is applied in any suitable manner as well known in this art. The coating is applied as a solution of a polymerizable hydrogel. Preferably isocyanate-functional or thiocyanate functional prepolymers are used that are prepared from relatively high molecular weight polyoxyalkylene diols or polyols by reacting them with difunctional and polyfunctional isocyanate or thiocyanate compounds. Although only polyfunctional (e.g. trifunctional) isocyanates or thiocyanates might be used, mixtures of these with difunctional molecules are generally employed. Polyurethane-based, isocyanate-functional hydrogels of this very general type are described in U.S. Pat. No. 3,939,123 (Mathews, et al.), U.S. Pat. No. 4,110,286 (Vandegaer, et al.) and U.S. Pat. No. 4,098,645 (Hartdegan, et al.).

Preferred prepolymers are ones made from polyoxyalkylene diols or polyols that comprise homopolymers of ethylene oxide units or block or random copolymers containing mixtures of ethylene oxide units and propylene oxide or butylene oxide units. In the case of such block or random copolymers, at least 75% of the units are preferably ethylene oxide units. Such polyoxyalkylene diol or polyol molecular weight is preferably from 500 to 30,000 daltons; it should be understood that molecular weight stated for polymers such as these are average molecular weights. In some instances, a polymer having a molecular weight of at least about 2,000 daltons is more preferred, and those having a MW of about 6000 to 7000 daltons may be particularly preferred. Suitable prepolymers may be prepared by reacting selected polyoxyalkylene diols or polyols with a polyisocyanate so that essentially all of the hydroxyl groups are capped with polyisocyanate, as described in more detail hereinafter. Generally, polyethylene glycol (PEG), polypropylene glycol (PPG) or copolymers thereof are preferred. The preferred isocyanate-functional prepolymers to be used for coating will contain active isocyanates in an amount of about 0.1 meq/gm to about 1 meq/gm, and more preferably about 0.2 meq/gm to about 0.8 meq/gm. If relatively low molecular weight prepolymers, e.g. substantially less than 2,000 daltons, are used, they are preferably formulated to contain a relatively high isocyanate content (about 1 meq/g or slightly higher). However, prepolymers with a particularly high isocyanate content may have a relatively high content of free amines after polymerization, and the positive charges on such amine functionalities, at neutral pH, may potentially increase non-specific binding of negatively charged biomolecules and require more stringent washing. Thus, higher molecular weight prepolymers which contain an isocyanate content in the range of about 0.2 to 0.8 meq/gm may generally be preferred.

Such high molecular weight prepolymers are often prepared by either of two general methods, but others as known in this art can also be used. In one method, a polyol (triol or higher) having a molecular weight of at least 2000 daltons is reacted with a polyisocyanate, such as isophorone diisocyanate (IPDI). In the other method, a diol having a molecular weight of at least 2000 daltons is reacted with a polyisocyanate and a cross-linking agent, such as glycerol, trimethylolpropane (TMP), trimethylolethane, triethanolamine or an organic triamine.

Aromatic, aliphatic or cycloaliphatic polyisocyanates may be used. High molecular weight, aliphatic isocyanate-capped prepolymers typically gel to a hydrated polymer state in about 20 to 90 minutes, whereas prepolymers capped with aromatic polyisocyanates gel much more rapidly. Examples of suitable bi- and multi-functional isocyanates are as follows: 4,4'-methylenebis-(phenyl isocyanate) (MDI), toluene-2,4-diisocyanate, toluene-2,6-diisocyanate (a mixture of which isomers is commercially sold as TDI), isophorone diisocyanate (IPDI), ethylene diisocyanate, ethylidene diisocyanate, propylene-1,2-diisocyanate, cyclobexylene-1,2-diisocyanate, cyclohexylene-1,4-diisocyanate,-phenylene diisocyanate, 3,3"-diphenyl-4,4"-biphenylene diisocyanate, 1,6-hexamethylene diisocyanate, 1,4-tetramethylene diisocyanate, 1,10-decamethylene diisocyanate, cumene-2,4-diisocyanate, 1,5-naphthalene diisocyanate, methylene dicyclohexyl diisocyanate, 1,4-cyclohexylene diisocyanate, p-tetramethyl xylylene diisocyanate, p-phenylene diisocyanate, 4-methoxy-1,3-phenylene diisocyanate, 4-chloro-1,3-phenylene diisocyanate, 4-bromo-1,3-phenylene diisocyanate, 4-ethoxyl-1,3- phenylene diisocyanate, 2,4-dimethyl-1,3-phenylene diisocyanate, 2,4-dimethyl-1,3-phenylene diisocyanate, 5,6-dimethyl-1,3-phenylene diisocyanate, 1,4-diisocyanatodiphenylether, 4,4'-diisocyanatodi-phenylether, benzidine diisocyanate, 4,6-dimethyl-1,3-phenylene diisocyanate, 9,10-anthracene diisocyanate, 4,4'-diisocyanatodibenzyl, 3,3'-dimethyl-4,4'-diisocyanatodiphenylmethane, 1,6-dimethyl-4,4'-diisocyanatodiphenyl, 2,4-diisocyanatostibene, 3,3'-dimethoxy-4,4'-diisocyanatodiphenyl, 1,4-antracenediisocyanate, 2,5-fluoronediisocyanate, 1,8-naphthalene diisocyanate, 2,6-diisocyanatobenzluran, 2,4,6-toluene triisocyanate, p,p',p"-triphenylmethane triisocyanate, trifunctional trimer (isocyanurate) of isophorone diisocyanate, trifunctional biuret of hexamethylene diisocyanate, trifunctional trimer (isocyanurate) of hexamethylene diisocyanate, polymeric 4,4'-diphenylmethane diisocyanate, xylene diisocyanate and m-tetramethyl xylene diisocyanate.

Capping of the selected diols or polyols with polyisocyanates to form prepolymers may be effected using stoichiometric amounts of reactants. The isocyanate-to-hydroxyl group ratio may vary as known in this art; however, it should preferably be about 1 to about 3, and more preferably about 1.2 to about 2.2. The capping reaction may be carried out using any suitable conditions, such as at about 20° C. to about 150° C., under dry nitrogen, for about 2 hours to about 14 days, and preferably in the absence of a catalyst. The preferred temperature is about 60° C. to 100° C., and the reaction terminates when the isocyanate concentration approximates theoretical values.

Preferred prepolymers include PEG that is end-capped with toluene diisocyanate; a copolymer of ethylene oxide and propylene oxide (optionally with trimethylolpropane) and toluene diisocyanate; toluene diisocyanate-polyethylene glycol-trimethylopropane, methylene diisocyanate-methylene homopolymer; polymeric methylene diisocyanate-polyethylene glycol; polymer of ethylene oxide-propylene oxide-trimethylolpropane and isophorone diisocyanate, and polyethylene glycol trilactate and toluene diisocyanate. Prepolymers meeting the above criteria can be obtained from Dow Chemical Company as HYPOL™ PreMA G-50, HYPOL 2000, HYPOL 3000, HYPOL 4000 and HYPOL 5000, which formulations generally include copolymers of polyethylene oxide and a minor amount of polypropylene oxide. Other prepolymers are available under the trademark Urepol from EnviroChem Technologies; moreover, comparable prepolymers can be prepared from commercially available feedstocks and may be preferred in order that more precise desired end specifications are achieved.

All things considered, the main chain of the hydrogel polymer is preferably comprised of residues of PEG, PPG, or a copolymer of PEG and PPG. The non-ionic, hydrophilic properties of polyethylene glycol and polypropylene glycol hydrogels provide for low levels of non-specific binding of biomaterial to the hydrogel and also provide good compatibility with sequestering agents, such as Abs, that are immobilized therewith, allowing them to maintain their native conformations and bioreactivity and thus promoting efficient capture.

As a particularly preferred embodiment, microparticle substrates are coated with an isocyanate-functional hydrogel that is based on a diol or triol of a high molecular weight polyethylene oxide, polypropylene oxide, or a copolymer of polyethylene oxide and polypropylene oxide, capped with water-active diisocyanates, and optionally lightly crosslinked with a suitable crosslinker. It is preferred that the quantity of active isocyanates present in the prepolymer is preferably between about 0.2 and about 0.8 meq/gm. Aromatic-based diisocyanates, such as TDI and MDI, may be mixed with an aliphatic diisocyanate, e.g. IPDI, or IPDI may be used alone. The formulation is designed so that, when attachment of a coating layer to the solid substrate is completed, only about 15% or less of the reactive isocyanates in the prepolymer will have reacted, which leaves ample isocyanate sites remaining (i.e. at least about 85%) for effecting the final polymerization and for either then or subsequently immobilizing the sequestering agents by direct or indirect covalent bonding. The prepolymer will usually be preformulated in a water-miscible organic solvent, and final polymerization generally takes place as a result of the formation of urea linkages which occurs following the simple addition of water.

If the spheroidal substrates which are chosen are made of hydrophobic material, one may experience difficulty in coating them using an aqueous coating solution, and when this is the situation, these hydrophobic spheroids are preferably first coated with a protein or the like that will render the surfaces hydrophilic, as by soaking them in an aqueous solution of casein or dried milk solids. The bead spheroidal surfaces can also be rendered hydrophilic by treatment in a plasma chamber for about three minutes; however, such hydrophilicity is transient, so they would need to be coated with the hydrogel solution shortly thereafter for such to be effective.

When it is desired to fashion beads substantially entirely of hydrogel, rather than simply coating commercially available beads, the same hydrogel prepolymer formulation as generally described above may be employed, preferably employing PPG, PEG or a copolymer thereof having a molecular weight of between about 3,000 and 15,000. Beads are created by providing a reservoir of an immiscible liquid, such as mineral oil, and using a standard stir bar or the like to stir it at a speed of about 100-300 rpm, e.g. about 200 rpm, at room temperature. A solution containing about 3 weight % of the prepolymer, having an active isocyanate content between about 0.2 and about 0.8 meq/gm, in an organic solvent, such as acetonitrile (Acn) and/or N-methyl-2-pyrrolidone (NMP), is added, as by pumping through an orifice preferably at a steady rate of flow. For example a syringe pump can be caused to discharge the solution, which preferably includes the sequestering agents or intermediate linkers, at a flow rate of about 1 mm/min through an orifice of about 100 microns internal diameter (ID). Generally the velocity at which the mineral oil is moved past the discharge orifice and the ID of the orifice determines the size of the hydrogel beads, as the droplets are broken off at the tip of the orifice. The droplet moves very quickly away from the orifice in the moving current of the mineral oil, and a sufficiently large reservoir is employed so that the droplets gel substantially independently into spheroidal beads without aggregating. After all of the polymer solution has been injected into the mineral oil reservoir, the rotation of the oil may be stopped. The beads are allowed to simply settle and cure, as the polymerization reaction proceeds via the formation of urea bonds within the prepolymer material, and spheroids of hydrogel result. After about 2 hours at room temperature after injection into the oil reservoir, substantially complete curing has been effected.

This procedure can be employed to fashion hydrogel beads which are spheroids between about 50 microns to 3 mm in size by regulating the size of the discharge orifice, the rate of exit flow from the orifice, and the velocity of the immiscible liquid being caused to flow therepast. Although any liquid that is considered to be a biologically suitable and substantially immiscible with the prepolymer solution may be used, mineral oil is readily available and is the preferred gelling medium. After separation from the gelling medium, the spheroids may be, and preferably are, retained in an aqueous environment, as by washing with PBS containing a small amount of Tween or the like to remove substantially all of the mineral oil and then storing the hydrated beads in water for any reasonable amount of time. Alternatively, the beads, following washing to remove the mineral oil, can be dried as by subjecting them to a stream of air for about 30 minutes and then stored at room temperature; they can be easily rehydrated when they are to be used. Whenever the beads are being created for a specific separation purpose so that the sequestering agents that are to be employed are known, they are included as a part of the formulation that is pumped through the discharge orifice as explained further hereinafter. When the beads are formed with sequestering agents, such as Abs, they are preferably thereafter maintained in the hydrated state until use so as not to risk denaturation of the Abs.

When the particular sequestering agent to be carried by the particles is known at the time that coating is carried out or that beads are being created from hydrogel, the hydrogel formulation that is used preferably contains an admixture of such sequestering agents dispersed uniformly throughout, and direct covalent bonding via the reactive isocyanate groups takes place as polymerization of the hydrogel is occurring. However, sequestering agents can also be attached to precoated beads or hydrogel beads. Alternatively, intermediate agents or moieties may instead be attached, preferably covalently, during polymerization, which agents are then used to indirectly anchor the desired specific sequestering agents. Such intermediate agents or moieties may be conveniently dissolved in aqueous solution and mixed with a prepolymer when the polymerization reaction is ready to begin, and they may be chosen so as to likewise covalently bind to the polymer through the isocyanate groups. In instances where sequestering agents, such as Abs, are to be bonded to hydrogel beads or to hydrogel-coated beads after such hydrogel has been polymerized and dried, the dried beads are preferably first rehydrated by treating with PBS at room temperature for 30 minutes.

Any appropriate sequestering agents that will selectively bind with high affinity to the target cells may be used. Although antibodies (Abs) are preferred, other sequestering agents that may be employed include lectins, receptor ligands, carbohydrates, hormones and similar molecules. When Abs are employed as the sequestering agents, if they would not naturally readily covalently bind with the reactive moities, e.g. NCO, that are present in the hydrogel coating, the Abs are preferably initially modified so as to so react, e.g. as by thiolation.

Procedures for generally covalently bonding antibodies to solid supports are described, for example, by Ichiro Chibata in IMMOBOLIZED ENZYMES, Halstead Press: New York (1987) and by A. Cuatrecasas, *J. Bio. Chem.* 245:3059 (1970), the contents of which references are hereby incorporated by reference. They indicate that Abs can be bound either directly or indirectly via intermediate linkers, e.g. using biotin-avidin or using some other species Abs. There are numerous such pairs well known in the art.

As one example of employing an antibody as a linker, Mueller et al. (*Lancet,* 336:197-200 (1990)) describe a method of isolating placenta-derived trophoblast cells from the blood of pregnant women using magnetic beads precoated with sheep antibody to mouse IgG (Fc fragment), which are incubated overnight at room temperature with a monoclonal antibody hybridoma culture supernatant. The blood from the pregnant women was collected into tubes, and it was incubated overnight with the antibody-coated beads, causing the desired cells to bind to the antibody on the beads. It is indicated that similar techniques can utilize antibodies to cell surface antigens present on any desired target fetal cells and not present on maternal cells.

An example of using a pair of coupling intermediates is described by R. J. Berenson et al., *J. of Immunol. Methods,* 91 (1986), in which the high affinity between the protein avidin and the vitamin biotin is exploited to create an indirect immunoadsorptive procedure. Using this technique, avidin was linked to cyanogen bromide-activated Sepahrose beads, washed in an alternating fashion with a coupling buffer and a washing buffer, and then stored at 4° C. Blood cells were incubated with 1) murine monoclonal antibody, and 2) biotinylated goat anti-mouse immunoglobulin. The treated cells were passed through a column packed with such beads in phosphate-buffered saline containing 2% bovine serum albumin (BSA). As another example, a procedure for conjugating biotin to an antibody is also described in Edward A. Bayer et al., "The Avidin-Biotin Complex in Affinity Cytochemistry", in *Methods in Enzymology, Vol.* 62 (1979). Other methods for conjugating antibodies to beads are exemplified in Thomas, T. E., et al., *J. of Immuno. Methods,* 120:221-131 (1989) and in deKretser, T. A., et al., *Tissue Antigens,* 16:317-325 (1980), all of which articles are incorporated herein by reference.

Although the use of such antibody-bound, hydrogel or hydrogel-coated beads does not require the preliminary isolation of any fraction from whole blood or the like, optional pretreatment to reduce volume and/or to remove other biomaterials may be optimally employed.

Very generally, the hydrogel or hydrogel-coated beads with the sequestering agents, such as antibodies, covalently bonded thereto may be used in any manner as such beads have been heretofore used for the separation or isolation of cells or other similar biomolecules from liquids, such as bodily fluids, e.g. human blood, urine, sputum, etc. Likewise, they may be used to sequester substantially any variety of target cells, including stem cells, cancer cells, fetal cells including platelets, trophoblasts, erythrocytes, leucocytes, etc. Antibodies having specificity for particular ligands which are found on the outer surfaces of human cells have been developed over the past several decades and are thus available for use in such isolation procedures.

The hydrogel-coated beads in their dry state will generally have a size range between about 10 microns and about 500 microns in diameter. However, for the isolation of desired target cells from human blood or the like, the preferred size range is between about 200 microns and about 400 microns. The substrate spheroids, of course, essentially constitute the size range of the ultimate bead product, because the coating which is applied will usually be only between about 0.1 micron and about 2 microns thick, and preferably about 1 micron thick in the dry state. When these coated particles are exposed to an aqueous environment, the hydrogel will swell, and the thickness of the coating may expand by at least about 3 times, and perhaps to a thickness of about 5 times or more than its thickness in the dry bead state. It should also be recognized that, in the swollen state, the exterior surface is far from smooth, but it is instead highly irregular, highly porous and constituted by a major portion of water which is bound to the hydrophilic polymer. Thus, the resultant coated product, when swollen in the presence of water, has an outer surface that is primarily constituted of water, and the polymer occupies only a minor percentage of the total volume of the region. The end result is an exterior layer or region that is highly porous so that ligands can freely pass into and out of this region.

When beads are produced substantially entirely of hydrogel, again the preferred size range is between about 200 microns and 400 microns in the hydrated state, and the production process is regulated so as to produce spheroids in this size range. If the hydrogel spheroids are not produced with sequestering agents covalently bonded thereto, they may be dried. Hydrated hyrogel beads of 200 to 400 microns, when dry, may be about 40 microns or less in size. As earlier indicated, they may be easily rehydrated by soaking in water or PBS, or by soaking in an aqueous solution containing a sequestering agent, at room temperature for at least about 30 minutes.

The free isocyanate groups which are present in the hydrogel provide the mechanism for covalently linking the sequestering agents, either directly or indirectly, to the beads. As previously indicated, the hydrogel preferably employed is one which has a high density of reactive isocyanate groups, and as a result, the beads have a ready propensity for affixing a large number of individual sequestering agents to a single bead, which of course is important to achieve efficiency in the separation of cells, and particularly rare cells, from human blood or the like. In this respect, an antibody density of about 3.6 to 18 micromole per mg of beads can be achieved using hydrogel or hydrogel-coated beads having an outer diameter in the range of about 10 to 500 microns. Our preferred size range of beads from about 200 to about 400 microns will generally have an Abs density of about 7 to about 9 micromole per mg of beads. Very generally, the greater the density of sequestering agents attached to the beads, the greater will be the efficiency of the isolation procedure in terms of percentage of specific cells captured from the total number of such cells in the sample being treated.

The following examples provide illustrations of the fabrication and use of hydrogel-coated beads and hydrogel beads embodying various features of this invention; however, they should, of course, be considered as illustrative only, because the scope of the invention is defined in the claims appended hereto. Moreover, comparative examples are also included wherein that the same or similar antibodies were bonded to prior art beads and used in similar separation procedures; these are included to provide comparisons to illustrate the unexpected efficiency of cell separation that is achieved by beads created in the described manner having a hydrogel exterior surface and the properties described hereinbefore and to also illustrate that far less nonspecific binding occurs.

COMPARATIVE EXAMPLE 1

Antibody Coated Duke Beads

Step i: Preparation of Thiolated Polystyrene Beads:

Polystyrene beads were obtained from Duke Scientific Corporation which are spheroids that have diameters of about 200 microns. The beads (0.5 g) were thiolated with triethoxysilylpropane thiol following a 5 minute plasma treatment to prepare their surfaces. After washing the beads with ethanol (3×2 ml), the thiolated beads were stored in 5 mM EDTA in 0.1 M HEPES buffer at 4° C.

Step ii: Activation of Antibody with Sulfo-LC-SMCC

CD71 antibody (0.2 mg in 200 µl buffer) (purchased from Leinco Technology), was concentrated to a volume of about 20 µl on Amicon microcon concentrator C-30 at 5000 RPM at 4° C. The retentate was dissolved in 200 µl of 0.2M MOPS/0.5M NaCl (pH 7.0) and again centrifuged as above to about 20 µl volume. After diluting to 90 µl with pH 7 MOPS buffer, the antibody was treated with 10 µl of 20 mM sulfo-NHS-LC-SMCC (Pierce) in DMF for 1 hour at room temperature (RT) with gentle shaking. The excess reagent was then neutralized with 25 µl of 100 mM glycine, followed by concentration of the reaction products on a C-30 concentrator to remove the neutralized sulfo-NHS-LC-SMCC.

Step iii: Conjugation of Antibody with Beads:

The resulting maleimido-CD71 was conjugated to about 10 mg of thiolated Duke beads in a total volume of 200 µl at pH 7.0 at RT for 15-16 hours. The antibody-coated beads were washed extensively to remove any unconjugated maleimido-CD71 and then stored at 4° C. in 20 mM PBS containing 1% BSA. They are hereinafter referred to as CB#1.

COMPARATIVE EXAMPLE 2

Antibody Coated Beads Through Streptavidin-Biotin Interaction

Step i: Modification of Streptavidin:

Strepavidin (1 mg, 6.7 nanomoles) was treated with 25 mM sulfo-NHS-LC-SMCC (10 µl) in a total volume of 200 µl of 0.2 M MOPS/0.5 M NaCl, pH 7.0, containing 10% DMF, at RT for 2 hours. After neutralizing the excess SMCC reagent by reaction with 20 µl of 100 mM glycine for 20 minutes, the reaction mixture was concentrated three times on a C-30 concentrator, each time using 200 µl of MOPS buffer to purify maleimido-streptavidin which was then stored in 200 µl of PBS/BSA, pH 7.0

Step ii: Conjugation of Maleimido-Streptavidin with Thiolated Beads:

Thiolated beads (10 mg) were suspended in 100 µl of pH 7.0 MOPS buffer and treated with 20 µl (0.2 mg) of maleimido-streptavidin at RT for 16 hours with gentle shaking. The resulting streptavin-coated beads were washed with 0.1 M HEPES/0.15 M NaCl containing 0.1% Triton X-100 and stored in PBS/BSA buffer at 4° C.

iii.: Preparation of Antibody-Coated Beads:

Biotinylated CD71 (100 µg), bought from Leinco Technology, was incubated with 10 mg of strepavidin-coated beads at pH 7.0 in 0.1 M HEPES/0.15 M NaCl (300 µl) for 2 hours at RT. The beads were then washed 3 times with 0.1% Triton X-100 in 0.1M HEPES buffer (pH 7.0) at 37° C. for 30 minutes, each time using 500 µl of the buffer. The antibody-coated beads were then stored in PBS/BSA buffer at 4° C. They are hereinafter referred to as CB#2.

COMPARATIVE EXAMPLE 3

Coating of Argonaut's Thiolated Polystyrene Beads with CD71

A. Preparation of Antibody-Coated Beads Through Biotin-Streptavidin Interaction:

Dithiolated beads, 150-200 µm, are obtained from Argonaut Technologies, Inc.; 100 mg of these beads were conjugated to maleimido-streptavidin (5 mg) following procedures of Comparative Example 2. Subsequent incubation of these streptavidin-coated beads with biotinylated-CD71 (Leinco) resulted in antibody-coated beads. The beads were extensively washed three times with 0.1 M HEPES buffer, pH 7.0, containing 0.1% Triton X-100 at 37° C. for 30 minutes each. These beads were stored in 20 mM PBS containing 1% BSA at 4° C. These beads are hereinafter referred to as CB#3A.

B. Covalent Conjugation of CD71 to Dithiolated Argonaut's Beads:

CD71 antibody was first modified with sulfo-NHS-LC-SMCC as described in Comparative Example 2. The resulting maleimido-CD71 was then covalently conjugated to the dithiolated beads using Comparative Example 2 procedures. After washing and purification, CD71-coated beads were obtained which were stored in 20 mM PBS and hereinafter referred to as CB#3B.

C. Trop 2-Coated Argonaut's Dithiolated Polystyrene Beads:

Thiolation of Trop 2 (0.2 mg), an antibody specific for antigens on fetal trophoblast cells, was effected using 20 fold excess of sulfo-NHS-LC-SMCC in 0.2 MOPS/0.5 M NaCl, pH 7.0 at RT for 1 hour and resulted in maleimido-Trop 2. The modified antibody was subsequently conjugated to dithiolated polystyrene beads; following purification, the beads, with the covalently bound Trop 2, were referred to as CB#3C.

Attempted Capture of Fetal Nucleated Red Blood Cells from Maternal Blood:

Blood (4 ml) from a normal adult male or female was spiked with cord blood (1 ml) from a normal first trimester pregnancy (8-12 weeks gestation) that was therapeutically terminated for social indications. After centrifugation, the plasma layer was removed and replaced with phosphate-buffered saline (PBS) containing 1% fetal calf serum. The blood was lysed with lysis buffer (50 ml), comprising 155 mM $NH_4Cl$, 2 mM EDTA, 0.55 mM $NH_4HCO_3$, and 10 µM acetazolamide at RT for 8-10 minutes, resulting in the lysing of adult RBCs. The suspension was then centrifuged at 13,000 RPM for 10 minutes. The supernatant was removed, and the cell pellet was resuspended in PBS (7 ml) and loaded onto a Histopaque column prepared by layering 2.5 ml of histopaque 1119 followed by sequential layering of Histopaques 1107 and 1077 (2.5 ml each). The supernatant and the layer of red blood cells above and for 0.5 ml into the 60% Percoll layer were carefully removed and discarded. The remaining gradient and the cell layer between 60% and 100% Percoll were diluted with PBS and spun at 13,000 RPM for 10 minutes. The supernatant was discarded. The cell pellet, suspended in HAM's F-12 media (200 µl), was used within 1 hour to study the cell capture by CD71-coated beads, i.e. CB#1, CB#2, CB#3A and CB#3B, using protocol set forth hereinafter.

A. General Protocol for Fetal nRBCs Capture:

50 µl of the above cell suspension was carefully added to each of the groups of CD71-coated beads (4 mg) in 100 µl of PBS/BSA. Each suspension was slowly and gently rotated on a wheel for about 1 hour at 4-8° C. After washing (3×, 500 µl PBS/BSA), the beads were examined under a fluorescence microscope. None of the groups of beads, i.e. CB#1, CB#2, CB#3A and CB#3B were found to have captured any significant number of fetal nRBCs.

COMPARATIVE EXAMPLE 5

Attempted Capture of Fetal Trophoblasts From Isolated from Cervical Mucous within the First Trimester:

Cervical mucous from a pregnant woman (8-12 weeks gestation) was diluted to 10 ml with HAM's media and treated with N-acetyl-L-cysteine (100 ng/ml) at RT for 45 minutes. The cell suspension was then treated with DNAse (120 units) at 37° C. for 30 minutes to break up mucous clumps. After filtering through a 100 µm cell strainer, the cell suspension was spun. The resulting cell pellet was suspended in HAM's media (200 µl) and incubated with beads (~15 mg) in a total volume of about 250 µl for about 1 hour at 4-8° C. with gentle mixing. After washing with PBS/BSA (3×200 µl) the beads were analyzed under a fluorescence microscope. No significant number of cells were captured on Trop 2-coated CB#3C beads.

COMPARATIVE EXAMPLE 6

Dynabeads™ are obtained from Dynal Biotech which are magnetic spheroids that have diameters of about 1-2 µm microns. The beads have been treated by the manufacturer to carry nRBC-specific monoclonal/polyclonal Abs on their exterior surfaces. These beads are used to attempt to isolate nRBCs from a sample of maternal blood following essentially the same procedure as described in Comparative Example 4. About 2 mg of antibody-coated Dynal beads are mixed with an nRBC-enriched blood sample of about 100 µl and incubated for about 1 hour at RT. The beads (CB#6) are then washed as before and examined microscopically. The number of nRBCs isolated is about 5-10% of the amount added for enrichment, which is considerably poorer than the performance of Applicant's hydrogel surface beads. Moreover, several beads were frequently found to bind to a single nRBC, and it is often cumbersome to subsequently free cells from these small beads.

EXAMPLE 1

Polystyrene beads were obtained from Duke Scientific Corporation which are spheroids that have diameters of about 200 microns. The beads are not otherwise surface-treated by the manufacturer and, as a result, are hydrophobic. The beads (0.5 g) were first subjected to plasma activation and then aminated with 50% triethoxysilylpropaneamine in 5 ml of dry $CH_2Cl_2$. The beads were then washed with ethanol (3×2 ml) and water (3×2 ml).

The aminated beads were mixed with a solution containing 3 weight % of a hydrogel prepolymer plus a selective antibody of choice. For example, an initial solution is made containing about 12.5 milligrams of a prepolymer; the prepolymer is made by reacting PEG having a MW of about 6000 daltons, TMP and IPDI (about 0.15 mole TMP:about 3.1 moles IPDI; about 1 mole PEG) at 120° C. under dry nitrogen in the absence of a catalyst. The resultant urethane prepolymer is isocyanate-terminated and has a reactive isocyanate content of about 0.4 meq. per gram. The ratio of isocyanate to hydroxyl is about 1.3 to 1. This solution contains a premix of the prepolymer, NMP and $CH_3CN$ in a weight ratio of 1:3:3. About 4 microliters of a PBS solution of Trop1, an antibody that is specific for trophoblast cells and which is present at a concentration of 1 milligram per milliliter, and 32.5 µl of an aqueous borate buffer (pH 8.3) are mixed with this initial solution. The resultant solution containing the Abs was disposed in a 1.5 milliliter eppindorf tube with 200 milligrams of these beads and agitated. After about 3 hours, the polymerizing solution had coated all of the bead exterior surfaces. Examination showed that each of the beads was covered with a thin coating of hydrogel, and the Trop 1 Abs density was about 7 to 9 micromole per mg. of beads. They are hereinafter referred to as the B1 beads.

EXAMPLE 2

In order to produce satisfactory beads made entirely of hydrogel, a large crystalizing dish is filled with mineral oil, and a stir bar is set for 200 rpm. About 100 µl of a solution similar to that described in Example 1, containing about 3% of the prepolymer but instead containing 4 µl (1 µg) of a CD71 antibody at a concentration of about 0.25 mg/ml, is fed through a syringe pump for discharge into the oil bath through a needle having a opening of about 100 microns ID. The pump is operated to create a steady rate of flow of the aqueous solution exiting the orifice, e.g. 1 milliliter per minute (1 ml/min).

The velocity of the oil that is caused to move past the needle (by the action of the stir bar as described above) and the ID of the injection needle determine the size of the hydrogel droplets that break off at the tip of the needle. As each droplet is broken off, it moves away from the needle, and by using a sufficiently large crystalizing dish, the beads that are forming do not aggregate but remain substantially isolated from one another. After all of the polymer solution has been injected into the oil dish, the stirring rotation is halted, and the beads are allowed to settle and cure. By regulating the ID of the needle, the injection rate of prepolymer solution and the speed of the stir bar, these beads, which are substantially all hydrogel, range from about 50 microns to about 500 microns in diameter in size. After three hours time, the beads are collected, and the mineral oil is washed off. These beads present the antibodies at their exterior surfaces where the CD71 Abs retain their three-dimensional configuration and will be effective to capture cells by conjugating to the ligands on their surfaces to which the antibodies are specific; the CD71 antibody density is about 7 to 9 micromole per mg of beads. The coated beads may be stored at room temperature in hydrated condition for at least about 3 months if desired. They are referred to as the B2 beads.

EXAMPLE 3

Use of the Coated Beads of Example 1 to Isolate Specific Cells

A cell suspension of cells from cervical mucous substantially the same as that prepared in Comparative Example 5 was prepared. About 5 mg of B1 beads with the Trop 2 Abs bonded thereto were incubated with the cell suspension in a total volume of about 250 µl for about 1 hour at 4-8° C. with gentle mixing. The beads were washed with PBS/BSA (3×200 µl) and analyzed under microscope. About 95% of the trophoblasts were captured on Trop 2-coated beads showing a very substantial improvement upon the performance of the CB#3C beads which carried the same Abs.

EXAMPLE 4

Use of the Coated Beads of Example 2 to Isolate Specific Cells

50 µl of cell suspension substantially the same as that prepared in Comparative Example 4 was prepared. About 5 mg of B2 beads with the CD71 Abs bonded thereto were incubated with the cell suspension in a volume of PBS/BSA of about 100 µl for about 15 min at 4-8° C. with gentle mixing on a wheel. The beads were washed with PBS/BSA (3×500 µl) and analyzed under microscope. About 95% of the fetal nRBCs that were added for enrichment were captured on these CD71-coated beads, showing a very substantial improvement upon the performance of the CB#1, CB#2, CB#3A, CB#3B and CB#6 beads which carried the same Abs.

Although the invention has been described with respect to a number of different embodiments which include the best modes presently contemplated by the inventors, it should be understood that changes and modifications as would be obvious to one skilled in this art may be made without departing from the scope of the invention which is set forth in the claims appended hereto. For example, although particular hydrogel formulations were used, other hydrogels can alternatively be formulated in accordance with the overall teachings. Although there are advantages in the use of beads carrying all the same sequestering agents, in certain situations, beads carrying two or more different sequestering agents may be suitable. Moreover, although the usefulness to isolate cells has been stressed, these beads may also be used to capture other biomolecules by attaching appropriate sequestering agents.

The disclosures of all U.S. patents cited herein are expressly incorporated herein by reference. Particular features of the invention are emphasized in the claims which follow.

The invention claimed is:

1. Beads for capturing target cells from a bodily fluid, which beads comprise:
    spheroids of a size between about 5 µm and about 500 µm, said spheroids having an exterior hydrophilic hydrogel surface that is constituted of an isocyanate- or a thiocyanate-functional polymer containing residues of PEG, PPG, or a copolymer thereof that are polymerized by urethane bonds, and
    agents which are directly or indirectly bound to said hydrogel via isocyanate or thiocyanate groups of said polymer, wherein said agents can contact and bind ligands on the surfaces of said target cells.

2. Beads according to claim 1, wherein said PEG, PPG or copolymer thereof has an average molecular weight of about 2000-7000 daltons, and wherein said hydrogel contains crosslinking.

3. Beads according to claim 2, wherein said hydrogel is obtained by reacting polyoxyalkylene diols or polyols with difunctional or polyfunctional isocyanate or thiocyanate compounds.

4. Beads according to claim 1, wherein said hydrogel is a reaction product of reactant (a), which is an isocyanate containing at least a major portion of diisocyanates, with reactant (b), which is said PEG, PPG, or copolymer thereof, wherein the molecules of reactant (b) each contain two or more hydroxyl groups, and wherein the reactants are reacted at a ratio of isocyanate of reactant (a) to hydroxyl of reactant (b) of about 1.2 to about 2.2.

5. Beads according to claim 1, wherein said spheroids are solid polymeric substrates coated by said hydrogel, and wherein said hydrogel coating is at least about 1 micron thick in the dry state and swells to at least about 3 times its thickness in an aqueous environment.

6. Beads according to claim 1, wherein said spheroids are substantially entirely hydrogel and contain said agents dispersed substantially throughout.

7. Beads according to claim 1, wherein said agents are selected from the group consisting of antibodies, lectins, receptor ligands, carbohydrates, and hormones.

8. Beads according to claim 1, wherein said agents are selected from the group consisting of antibodies, lectins, receptor ligands, carbohydrates, and hormones, and wherein said agents retain their native 3-dimensional configuration.

9. Beads according to claim 1, wherein said agents are antibodies and said antibodies retain their native 3-dimensional configuration.

10. Beads according to claim 1, wherein said agents are indirectly bound to said hydrogel.

11. Beads according to claim 1, wherein said polymer is an isocyanate-functional polymer, and wherein said agents are directly or indirectly bound to isocyanate groups of said polymer.

12. A method for capturing target cells from a bodily fluid, which method comprises the steps of:
  (a) providing beads according to claim 1, and
  (b) bringing said beads into contact with said bodily fluid, so that said target cells are captured by binding to said agents that are specific to said target cells.

13. The method according to claim 12, wherein said spheroids are washed following step (b) to remove nonspecifically bound biomaterial so that substantially only the captured target cells adhere to said beads.

14. The method according to claim 12, wherein said PEG, PPG, or copolymer thereof has a molecular weight of about 6000-7000 daltons, and wherein said hydrogel contains crosslinking.

15. The method according to claim 12, wherein said hydrogel is a reaction product of reactant (a), which is an isocyanate and/or polyisocyanate, with reactant (b), which is said PEG, PPG, or copolymer thereof, wherein the molecules of reactant (b) each contain two or more hydroxyl groups, and wherein the reactants are reacted at a ratio of isocyanate of reactant (a) to hydroxyl of reactant (b) of about 1.2 to about 2.2.

16. The method according to claim 12, wherein said spheroids are solid polymeric substrates coated by said hydrogel, and wherein said hydrogel coating is at least about 1 micron thick when dry and swells to at least 3 times its thickness in an aqueous environment.

17. The method according to claim 12, wherein said hydrogel is obtained by reacting polyoxyalkylene diols or polyols with difunctional or polyfunctional isocyanate or thiocyanate compounds.

18. The method according to claim 12, wherein said spheroids are substantially entirely hydrogel and contain said agents dispersed substantially throughout.

19. The method according to claim 12, wherein said agents are selected from the group consisting of antibodies, lectins, receptor ligands, carbohydrates, and hormones.

20. The method according to claim 12, wherein said agents are selected from the group consisting of antibodies, lectins, receptor ligands, carbohydrates, and hormones, and wherein said agents retain their native 3-dimensional configuration.

21. The method according to claim 12, wherein said agents are antibodies and said antibodies retain their native 3-dimensional configuration.

22. The method according to claim 12, wherein said agents are indirectly bound to said hydrogel.

23. The method according to claim 12, wherein said polymer is an isocyanate-functional polymer, and wherein said agents are directly or indirectly bound to isocyanate groups of said polymer.

* * * * *